United States Patent [19]

Thompson

[11] Patent Number: 4,916,394
[45] Date of Patent: Apr. 10, 1990

[54] DEVICE FOR ADJUSTABLE MOUNTING OF MAGNETIC SENSING COILS USED IN PIPE INSPECTION

[75] Inventor: Carroll R. Thompson, Woodlands, Tex.

[73] Assignee: Scan Systems, Inc., Channelview, Tex.

[21] Appl. No.: 315,930

[22] Filed: Feb. 27, 1989

[51] Int. Cl.$^4$ .................. G01N 27/82; G01R 33/12
[52] U.S. Cl. ..................................... 324/262; 324/242
[58] Field of Search .................. 324/200, 217–221, 324/226, 234–243, 260–263; 73/622, 638

[56] References Cited

U.S. PATENT DOCUMENTS

| | | | |
|---|---|---|---|
| 3,170,114 | 2/1965 | Placke | 324/262 |
| 3,361,959 | 1/1968 | Placke | 324/262 X |
| 3,535,624 | 10/1970 | Wood | 324/226 |
| 3,568,049 | 3/1971 | Barton | 324/262 X |
| 4,543,528 | 9/1985 | Baraona | 324/262 |

Primary Examiner—Gerard R. Strecker

[57] ABSTRACT

An adjustable mounting shoe 10 for sensing coils 31 of a pipe inspection apparatus. The mounting shoe 10 comprises a base member 12 with a recess 14 in a surface thereof in which the magnetic sensing coils 31 are mounted. A thin shim 40 of magnetically transparent material is removably supported on the base member 12 in covering relationship to the sensing coils 31 whereby the coils are protected from abrasive contact with the exterior surface of a pipe to be inspected. A pair of adjustable contact members 51 are mounted on opposite sides of the recess 14 and provided with contact surfaces 51b positioned to engage the exterior surface of a pipe while supporting the magnetic sensing coils protected by the shim in an optimum sensing range from the surface of the pipe. Means (21,22,23,60) are provided for adjustably mounting each contact member 51 for selected movement towards or away from the recess 14 for accommodating use of the sensor shoe with pipes of different diameters while maintaining the sensing coils in optimum sensing distance. The shim 40 is also replaceable if it becomes worn down by abrasive contact through extensive use or if it is desired to use a shim of different thickness if a different coil sensing range is appropriate.

14 Claims, 2 Drawing Sheets

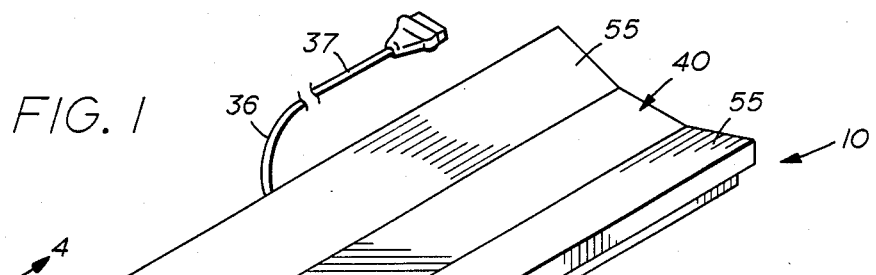
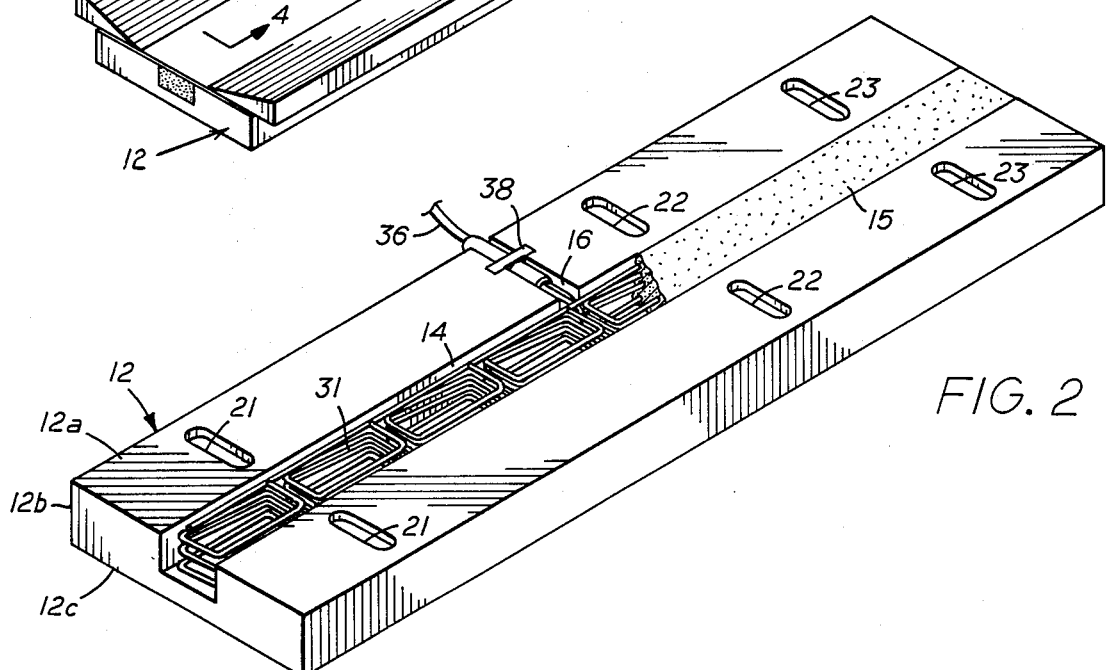
FIG. 1
FIG. 2
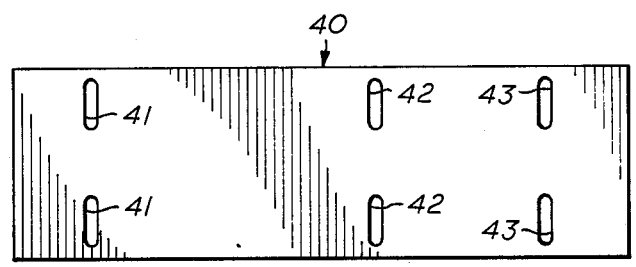
FIG. 3
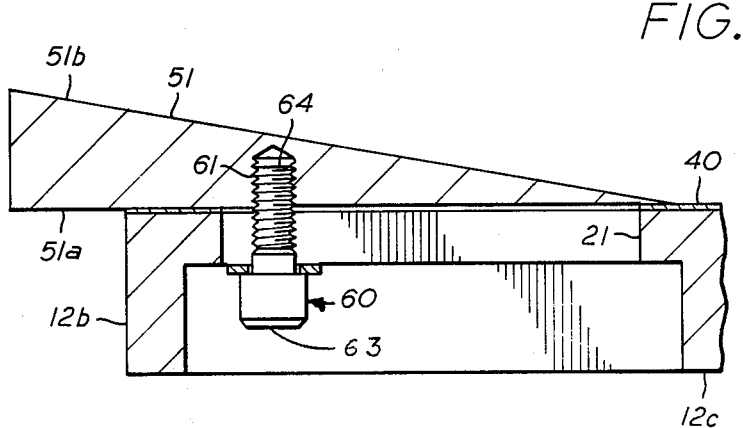
FIG. 4

DEVICE FOR ADJUSTABLE MOUNTING OF MAGNETIC SENSING COILS USED IN PIPE INSPECTION

FIELD OF THE INVENTION

This invention relates to magnetic pipe inspection apparatus, and more particularly to sensor shoes for mounting magnetic sensing coils which are used for sensing variations in a magnetic field in a tubular pipe member.

BACKGROUND ART

Inspection of metal pipe or tubular members by magnetic means conventionally involves magnetizing the member to create a magnetic field which extends circumferentially and is characterized by lines of magnetic flux which extend either axially of the tubular member or generally perpendicular to its axis, dependent on the manner by which magnetism is induced. In many of the present systems, current flow through a wire coil positioned about the tubular member forms magnetic lines of flux through the opening of the coil which extend axially of the member under inspection. In other systems, current flows axially of the tubular member within the wall thereof so as to create a magnetic field, the lines of flux of which extend circumferentially about the tubular member in an orientation substantially perpendicular to the tubular member. The presence of structural flaws or anomalies in the wall of the tubular member, such as surface nicks or pits, cracks, voids, or various crystalline discontinuities, disturbs the uniformity of a magnetic field in the wall of the tubular member. Accordingly, the structural integrity of the tubular member and its relative freedom of such flaws may be inspected by sensing and detecting the magnetic field variations with sensors disposed closely adjacent the surface of the tubular member.

The sensing of variations in a magnetic field in a pipe wall is customarily achieved by passing or moving an induction coil or similar device through the magnetic field and any magnetic field variations to induce voltages in the coil indicative of the magnetic field variations. The voltages or voltage signals may then be transmitted to appropriate recording and processing equipment. For optimum detection sensitivity and for detection of very small cracks in a pipe wall which can be a few thousandths of an inch in depth, it is necessary that the detecting or sensor coil be placed closely adjacent the exterior surface of the tubular member. Normally the adjacent coil is disposed from 0.002 inches (0.051 mm) to 0.020 inches (0.51 mm) relative the surface of the tubular member with the axis of the coil substantially perpendicular to the surface. The sensor coils are mounted in a support, conventionally referred to as a sensor shoe, which is provided with contact surfaces adapted to contact with the surface of the tubular member in a manner so that the sensing coil is supported closely adjacent the surface of the tubular member at an optimum distance or spacing. Normally, the coil is protected from direct contact with the surface of the pipe by means of a thin shim of magnetically transparent material.

Inspecting the surface of the tubular members requires that the inspection sensor be moved along the surface in a predetermined inspection path. In one widely used pipe inspection apparatus, a plurality of sensor shoes are applied to the surface of the pipe in circumferential spacing thereabout and each of the sensor shoes is moved relatively to the pipe in a circumferential helical path whereby the plurality of sensors provide more than 100 percent coverage of the pipe surface. The relative movement may be effected by moving the sensors longitudinally while rotating the sensor shoes around a stationary pipe or the pipe can be moved longitudinally while the sensors are rotated about the pipe. In any event, there is relative sliding movement between the sensor shoes and the pipe surface, which causes wear of the contact surfaces of a sensor shoe by extensive use. The shim also can come into contact with the pipe and can be similarly eroded. The wearing down of the contact surfaces and shim results in the coils being supported from the pipe surface inside the optimum spacing range or possibly being damaged by eventual contact with the pipe. When either event occurs, a new sensor shoe is required.

Furthermore, sensor shoes are customarily designed for use with a specific diameter of pipe, and the contact surfaces of a sensor shoe are fixed in a permanent orientation such that when placed in contact with the surface of the pipe, the sensing coil is positioned for optimum detection sensitivity. Accordingly, a given sensor shoe is designed for inspection of only one diameter of pipe and is inappropriate for use as an inspection sensor for pipes of a different diameter since for such pipe diameters the sensing coil is supported at other than an optimum distance from the surface to be inspected.

SUMMARY OF THE INVENTION

The invention relates to an adjustable mounting shoe for mounting magnetic sensing coils of a pipe inspection apparatus. The mounting shoe comprises a base member with a recess in a surface thereof in which the magnetic sensing coils are mounted. The mounting shoe includes a thin shim of magnetically transparent material which is removably supported on the base member in covering relationship to the magnetic sensing coils whereby the coils are protected from abrasive contact with the exterior surface of a pipe to be inspected. The mounting shoe is also provided with a pair of adjustable contact members mounted on opposite sides of the recess and provided with contact surfaces positioned to engage the exterior surface of a pipe while supporting the magnetic sensing coils protected by the shim in an optimum sensing range from the surface of the pipe. Further included are means for adjustably mounting each said contact member for selected movement towards or away from the recess and sensing coils for accommodating use of the sensor shoe with pipes of different diameters while maintaining the sensing coils in optimum sensing distance from the pipe. The protective shim is also readily removable and replaceable when it becomes desirable to replace the shim if it becomes worn down by abrasive contact through extensive use or to use a shim of different thickness if a different coil sensing range is appropriate.

BRIEF DESCRIPTION OF THE DRAWINGS

FIG. 1 is a perspective view of a sensor mounting shoe which represents a preferred embodiment of the invention for use in a pipe inspection apparatus;

FIG. 2 is a perspective view of the base member of the sensor mounting shoe of FIG. 1, showing an arrangement of magnetic sensing coils which are mounted thereon;

FIG. 3 is a plan view of a protective shim which in the assembly of the sensor mounting shoe is removably mounted on the base member of FIG. 2 in covering relationship to the sensing coils;

FIG. 4 is a sectional view taken along the section line 4—4 of FIG. 1 which shows a means for releasably and adjustably mounting the shim and pipe contact members of the sensor shoe of FIG. 1;

DETAILED DESCRIPTION OF THE INVENTION

Figure 5:
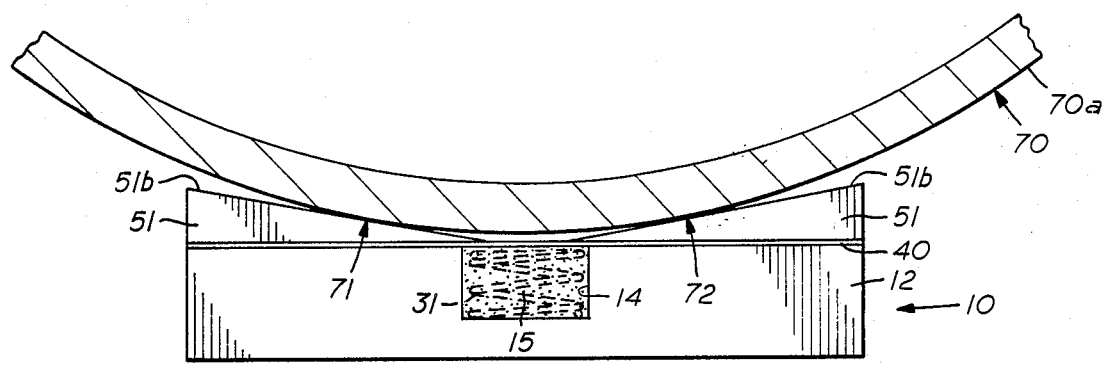
FIG. 5 is an end view of the sensor shoe of FIG. 1 showing the sensor shoe in operational contact with the exterior surface of a pipe which is to be magnetically inspected.

Referring more particularly to the drawings, there is shown in FIG. 1 an adjustable sensor mounting shoe 10 which illustrates a preferred embodiment of the invention. The reusable sensor shoe 10 comprises a base member 12 of nonmagnetic material, such as brass or the like. The base member 12 is preferably of elongate form with rectangular planar surfaces.

As shown in FIG. 2, one of the faces 12a of the base member is provided with a recess 14 extending the length of the base member 12 along the mid-line thereof and a transverse groove 16 which extends from a narrow side 12b of the base 12 to communicate with the recess 14. The base member 12 is also provided with three pairs of elongate slots 21, 22, 23 extending through the base member 12 from the face 12a to a bottom face 12c. As best seen in FIG. 2, the slots extend in a transverse direction with respect to the elongate recess 14 with the slots of each pair located on opposite sides of the recess 14 in axially aligned relationship with respect to one another.

A plurality of inductance coils 31 are fitted in the recess 14, positioned adjacent to one another throughout the length of the recess 14. Each coil is comprised of axially aligned wire turns with the coil axes disposed perpendicular to the plane of the surface 12a. For purposes relating to signal strength, sensitivity and the like, the number of coils located in the recess 14 may be a selected number and their particular positional relationship to one another may vary from the arrangement shown in FIG. 2. For example, some of the coils may be positioned in superimposed overlapping relationship to others. In addition the leads from the several coils 31 are brought together in the form of a cable 36 which is run through the transverse groove 16 and provided with a multi-pronged connector 37 for accommodating connection of the individual sensing coils to appropriate circuitry and equipment for recording and processing voltage signals from the coils. The cable 36 is also tightly clamped in the groove 16 by a suitable clamp means 38 which precludes damage to the coils 31 and the coil leads by inadvertent tension forces applied to the cable 36. The clamp 38 could be in the form of an insert in the face 12a or a screw.

For fixing the coils 31 in the recess 14, the recess 14 is filled with a magnetically transparent potting material 15, of epoxy or the like, which encases each of the coils and secures it in place. For further protecting the coils 31, the sensor shoe 10 is also provided with a thin metallic shim 40 of magnetically transparent material, such as stainless steel (see FIG. 3). The shim 40 is typically of a thickness in the range of 0.002 inches (0.051 mm) to 0.02 inches (0.51 mm) and is of a configuration conforming to that of the base surface 12a over which it is superposed in flush engagement. The shim 40 is also provided with three pairs of elongate slots 41, 42, 44 which are respectively disposed in registry with the slot pairs 21, 22, 23 of the base member 12.

Seated atop the flat surface of the shim 40 are a pair of elongate contact members 51 (see FIG. 4), each of triangular cross-section and provided with a flat surface 51a disposed in flush engagement with the surface of the shim 40 and a planar contact surface 51b angularly disposed and convergent therewith. Each of the contact members 51 is mounted on the shim 40 by three screws 60, the threaded shanks 61 of which extend through slots 41, 42, 43 of the shim 40 and slots 21, 22, 23 in the base member 12 which are in registry therewith and disposed on the same side of the recess 14. As shown in FIG. 4, each of the contact members 51 is provided with threaded blind bores 64 for accommodating connection with the screws 60 and each of the screws 60 is provided with a screw head 63 for clamping against the base member 12 on both sides of a slot 21, 22, or 23 in which it is disposed. By positioning the shank 61 of a screw 60 at a select location along the length of a slot 21, 22, or 23, a contact member 51 is adjustably mounted for movement in a transverse direction towards or away from the axis of the recess 14.

As shown in FIG. 5, the contact members 51 are symmetrically positioned on opposite sides of the longitudinal axis of the recess 14 at equal distances from the center of the recess 14. The particular distance selected is chosen to provide an optimum configuration of the sensor shoe 10 for use in inspecting a pipe of specific diameter. Preferably, the contact members 51 are of identical cross-section and similar configuration. The angle of convergence of the contact surface 51b with the bottom surface 51a is identical in each contact member and may be selected as desired. Typically, a large convergence angle requires a greater extension of the slots 21, 22, 23 and a wider base member 12.

As seen in FIG. 5, which shows a sensor shoe 10 in operational engagement with a pipe 70 about which a magnetic field has been created, the contact members 51 are positioned to provide two parallel lines of contact between the sensor shoe 10 and the pipe 70 (indicated by the points 71, 72) such that the shim 40 is closely adjacent the exterior surface 70a of the pipe 70, typically 0.002 inches (0.057 mm) therefrom at the center line of the coils. Since the coils 31 are generally in abutting relation with the shim 40, a very thin shim allows placement of the sensing coils in very close proximity to the surface of the pipe where it is possible to detection variations in magnetic flux caused by very small surface cracks with dimensions of a few thousandths of an inch.

In a configuration of the sensor shoe 10, as shown in FIG. 5, the sensor coils 31 are shown spaced at an optimum sensing range from the pipe 70. However, with extensive use, the contact surface of the contact members 51 (at points 70, 71) can be worn down and the shim 40 could come to contact the pipe and become abraded by frictional contact as the sensor shoe 10 moves relatively over the pipe in a magnetic inspection procedure. At this point of operation, replacement of the shim 40 and an adjustment of the contact members 51 to maintain optimum sensing range is therefore very desirable and is easy to accomplish. The shoe is reusable, only the shim and possibly the contact members 51 need be replaced.

Figure 6:
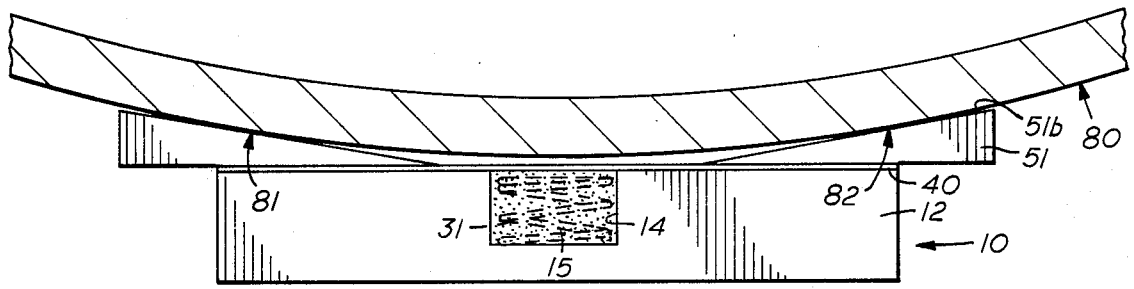
FIG. 6 is a view similar to FIG. 5 showing the sensor shoe in operational contact with a pipe of larger diameter and wherein the positions of the contact members of the sensor shoe relative to the base member have been adjusted to maintain an optimum sensing range of the sensing coils with respect to the pipe.

It is also to be noted that if the sensor shoe 10 of FIG. 5 is applied to a pipe of different diameter, the shim 40 and the sensing coils are likely to be at an inappropriate distance from the pipe for magnetic inspection purposes. In FIG. 6, the sensor shoe 10 is shown applied to a much larger diameter pipe 80. In order that the sensing coils in the recess 14 are in the optimum sensing range and the shim 40 spaced from the pipe surface by approximately 0.002 inches (0.051 mm), the contact members 51 are adjusted outwardly from the recess 14, establishing lines of contact 81, 82 with the pipe 80.

It will therefore be seen that a new and improved sensor mounting shoe for magnetic pipe inspection apparatus is disclosed herein. The sensor shoe is provided with pipe contacting members which may be adjustably positioned for accommodating the use of the sensor shoe for inspecting pipes of different sizes and a wide range of diameters. In addition, the parts of the sensor shoe which are likely to be worn down by extensive use, such as the contact members 51 and the shim 40 may be readily replaced, thereby effecting considerable economies in the conduct of magnetic pipe inspection operations. To minimize wear, the contact members 51 are made of hard material, such as tungsten carbide or beryllium-copper alloy.

It will therefore be seen that a new and improved sensor mounting shoe for application to the exterior surface of a pipe or tubular member of ferromagnetic material is disclosed herein. The shoe, which typically includes sensors for detecting variations in a magnetic field produced by direct or alternating current, can be readily adjusted for use with pipes or tubular members of a wide range of diameters. In addition, the parts thereof, which are normally disposed in contact with the pipe and are susceptible to wear with extensive use, and the protective shim, should it also become abraded, can be readily replaced.

It is also to be understood that the foregoing description of a preferred embodiment of the invention has been presented for purposes of illustration and explanation and is not intended to limit the invention to the precise form disclosed. For example, the base member could have a configuration, other than rectangular cross-section, and it is not essential that the contact members have planar contact surfaces for making contact with the curved exterior of the pipe. It is only essential that the contact members be adjustable so that contact can be made which will accommodate pipes of different diameter while maintaining an optimum sensing range for the sensing coils and optimum spacing for the protective shim.

It is to be appreciated therefore that various material and structural changes, many of which are suggested herein, may be made by those skilled in the art without departing from the spirit of the invention.

I claim:

1. A mounting shoe or support for a sensor inductance coil or coils which is used in an inspection apparatus for detection of structural flaws in a pipe of ferromagnetic material where such inspection is performed by inducing magnetization of the pipe and sensing variations in the magnetic field thereabout, said mounting shoe comprising:

a base member of non-magnetic material, said base member having at least one planar surface and an elongate recess formed in said planar surface;

a plurality of inductance coils mounted in said recess;

a shim in the form of a thin sheet of magnetically transparent material which is secured to said base in a position which covers said elongate recess and the inductance coils carried therein;

a pair of elongate contact members supported on said shim on both sides of said recess in generally symmetric relationship thereto, each of said contact members having a planar contact surface disposed at an angle to the planar surface of the base member and adapted for contact with the exterior surface of a pipe to be inspected; and means for adjustably mounting each said contact member for movement on said shim in a direction transverse to said recess whereby the contact members may be positioned on said shim at a selected distance from said recess appropriate for establishing lines of contact with said pipe surface on both sides of said recess such that the shim is closely adjacent the surface of the pipe and the inductance coils are at an optimum sensing range from said pipe surface.

2. A sensor mounting shoe as set forth in claim 1 wherein said shim is of a thickness in the range of 0.002 to 0.02 inches.

3. A sensor mounting shoe as set forth in claim 1 wherein said base member is further provided with a groove in said planar surface which connects with said elongate recess and the leads from said inductance coils are extended therethrough for connection to apparatus for recording and processing voltage signals from said inductance coils induced by variations in the magnetic field about said pipe indicative of structural flaws in said pipe.

4. A sensor mounting shoe as set forth in claim 1 wherein said inductance coils are encased and fixed in position in said recess by a magnetically transparent epoxy.

5. A sensor mounting shoe as set forth in claim 1 wherein each of said contact members is disposed on said shim with said planar contact surface thereof disposed in a direction of convergence with said shim which extends toward said recess and the other of said contact members.

6. A sensor mounting shoe as set forth in claim 1 including means for releasably and removably mounting the shim to said base member whereby said shim may be readily replaced.

7. A sensor mounting shoe for magnetic sensing coils which is used in an inspection apparatus for detection of structural flaws in a tubular member of ferromagnetic material where such inspection is performed by inducing magnetization of the tubular member and sensing variations in the magnetic field thereabout, said mounting shoe comprising:

a base member of non-magnetic material, said base member having a recess formed in one of the surfaces thereof;

one or more magnetic sensing coils mounted in said recess;

a shim in the form of a thin sheet of magnetically transparent material which is removably secured to said base surface in a position which covers said recess and the magnetic sensing coils mounted therein;

a pair of contact members supported on said shim on opposite sides of said recess in generally symmetric relationship thereto, each of said contact members having a contact surface adapted for contact with the exterior surface of a tubular member and disposed at an angle to the surface of the base member which includes said recess; and means for adjustably mounting each said contact member for movement on said shim in a direction directly towards or away from said recess whereby the contact members may be positioned on said shim at a selected distance from said recess which is appropriate for establishing contact with the surface of the tubular member on both sides of said recess such that the shim is closely adjacent the surface of the tubular member and the magnetic sensing coils are at an optimum sensing range.

8. A sensor mounting shoe as set forth in claim 7 wherein said shim is of a thickness in the range of 0.002 to 0.02 inches.

9. A sensor mounting shoe as set forth in claim 7 wherein said base member is further provided with an opening which extends from a surface thereof to connect with said recess and the leads from said sensing coils are extended therethrough for connection to apparatus for recording and processing voltage signals from said sensing coils induced by variations in the magnetic field about said tubular member.

10. A sensor mounting shoe as set forth in claim 7 wherein said magnetic sensing coils are encased and fixed in position in said recess by a magnetically transparent potting material.

11. A sensor mounting shoe as set forth in claim 7 wherein each of said contact members is disposed on said shim with said contact surface thereof disposed in a direction of convergence with said shim which extends toward said recess and the other of said contact members.

12. A sensor mounting shoe as set forth in claim 11 which includes means for removably mounting said shim and said contact members to the base member for accommodating replacement of the shim and contact members.

13. A sensor mounting shoe as set forth in claim 11 wherein said pair of contact members are made of tungsten carbide material.

14. A sensor mounting shoe as set forth in claim 11 wherein said base member is made of brass and said pair of contact members are made of beryllium copper alloy.

* * * * *